(12) United States Patent
McDonald et al.

(10) Patent No.: US 10,335,602 B2
(45) Date of Patent: Jul. 2, 2019

(54) HOLDER FOR AN IMPLANTABLE MEDICAL DEVICE

(71) Applicant: Boston Scientific Neuromodulation Corporation, Valencia, CA (US)

(72) Inventors: Matthew Lee McDonald, Pasadena, CA (US); Jillian Doubek, Los Angeles, CA (US); Samuel Tahmasian, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 36 days.

(21) Appl. No.: 15/631,890

(22) Filed: Jun. 23, 2017

(65) Prior Publication Data

US 2018/0015289 A1    Jan. 18, 2018

Related U.S. Application Data

(60) Provisional application No. 62/362,943, filed on Jul. 15, 2016.

(51) Int. Cl.
| | | |
|---|---|---|
| *A61N 1/05* | (2006.01) | |
| *A61N 1/08* | (2006.01) | |
| *A61N 1/375* | (2006.01) | |
| *A61N 1/378* | (2006.01) | |

(52) U.S. Cl.
CPC ............... *A61N 1/375* (2013.01); *A61N 1/05* (2013.01); *A61N 1/3787* (2013.01); *A61N 1/08* (2013.01)

(58) Field of Classification Search
CPC . A61N 1/05; A61N 1/08; A61N 1/375; A61N 1/3787

USPC ......................................................... 607/60
See application file for complete search history.

(56) References Cited

U.S. PATENT DOCUMENTS

| | | | |
|---|---|---|---|
| 3,654,933 A | 4/1972 | Hagfors | |
| 3,683,933 A | 8/1972 | Mansfield | |
| 5,443,065 A * | 8/1995 | Berghoff | .............. A61N 1/3625 439/380 |
| 6,006,135 A | 12/1999 | Kast et al. | |

(Continued)

OTHER PUBLICATIONS

International Search Report and Written Opinion regarding PCT application No. PCT/US2017/039251, dated Sep. 7, 2017.

*Primary Examiner* — Christopher A Flory
(74) *Attorney, Agent, or Firm* — Lewis & Reese, PLLC

(57) ABSTRACT

A holder for an implantable medical device (IMD) is disclosed. The holder is configured to hold the IMD in a single, operational orientation when the holder containing the IMD is implanted in a patient. The holder is designed to prevent the IMD from moving within the patient and shifting orientation. The holder may have an opening for receiving a connecting pin, for stimulating electrodes, for example, in a mating orientation with respect to a receptacle contained within the IMB. According to some embodiments, the IMB features a metal housing that can serve as an electrode and the holder is configured with a window to allow a portion of the housing to electrically contact flesh of a patient during operation. Holders for containing a single IMD and holders for containing multiple IMDs are disclosed. Holders for containing multiple IMDs are configured to maintain alignment of the IMDs with respect to each other, for example, a parallel alignment.

9 Claims, 5 Drawing Sheets

(56) References Cited

U.S. PATENT DOCUMENTS

| | | | |
|---|---|---|---|
| 6,096,064 A * | 8/2000 | Routh | A61N 1/056 607/9 |
| 6,192,278 B1 * | 2/2001 | Werner | A61N 1/3752 607/115 |
| 6,516,227 B1 * | 2/2003 | Meadows | A61N 1/0553 607/117 |
| 6,984,145 B1 * | 1/2006 | Lim | A61N 1/3752 439/462 |
| 7,054,692 B1 | 5/2006 | Whitehurst et al. | |
| 7,283,878 B2 * | 10/2007 | Brostrom | A61N 1/056 607/115 |
| 8,224,450 B2 | 7/2012 | Brase | |
| 8,321,029 B2 | 11/2012 | Aghassian | |
| 8,676,318 B2 | 3/2014 | Carbunaru et al. | |
| 9,364,672 B2 | 6/2016 | Marnfeldt | |
| 2002/0193858 A1 * | 12/2002 | Schulman | A61N 1/05 607/116 |
| 2002/0193859 A1 * | 12/2002 | Schulman | A61N 1/05 607/116 |
| 2005/0113894 A1 | 5/2005 | Zilberman et al. | |
| 2005/0234318 A1 * | 10/2005 | Schulman | A61N 1/05600/373 |
| 2005/0234533 A1 * | 10/2005 | Schulman | A61N 1/05 607/115 |
| 2006/0247748 A1 * | 11/2006 | Wahlstrand | A61N 1/0534 607/116 |
| 2008/0208301 A1 * | 8/2008 | Alexander | A61N 1/05 607/116 |
| 2010/0305663 A1 | 12/2010 | Aghassian | |
| 2012/0010689 A1 * | 1/2012 | Wahlstrand | A61N 1/0534 607/116 |
| 2013/0096652 A1 | 4/2013 | Ozawa et al. | |
| 2014/0163579 A1 * | 6/2014 | Tischendorf | A61N 1/36139 606/129 |
| 2014/0163580 A1 * | 6/2014 | Tischendorf | A61N 1/36139 606/129 |
| 2015/0190640 A1 * | 7/2015 | Przybyszewski | A61N 1/0551 607/62 |
| 2016/0175596 A1 * | 6/2016 | Pryzbyszewski | A61N 1/0551 607/62 |
| 2017/0014635 A1 * | 1/2017 | Villarta | A61N 1/3752 |
| 2017/0027620 A1 * | 2/2017 | Dinville | A61B 17/7065 |
| 2017/0216604 A1 * | 8/2017 | Villarta | A61N 1/3752 |
| 2017/0239460 A1 * | 8/2017 | Przybyszewski | A61N 1/0551 |

\* cited by examiner

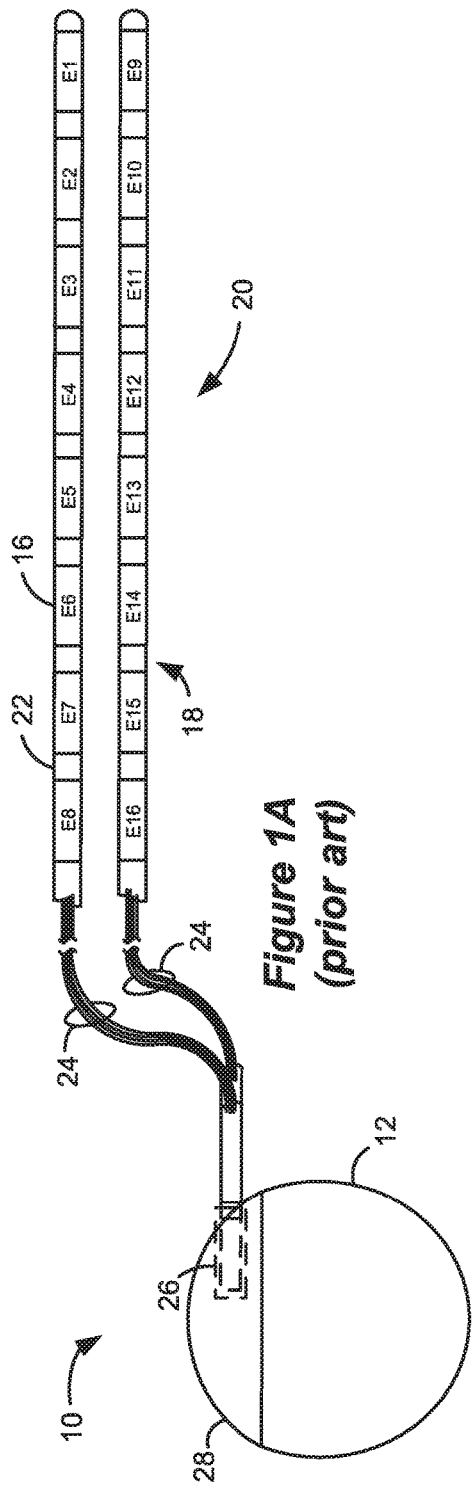
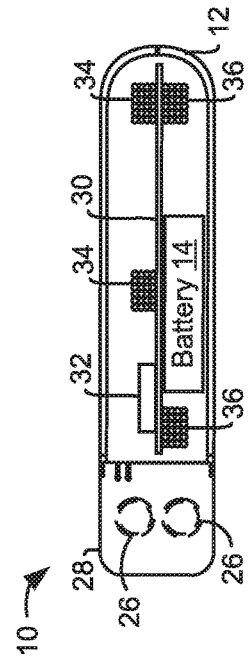
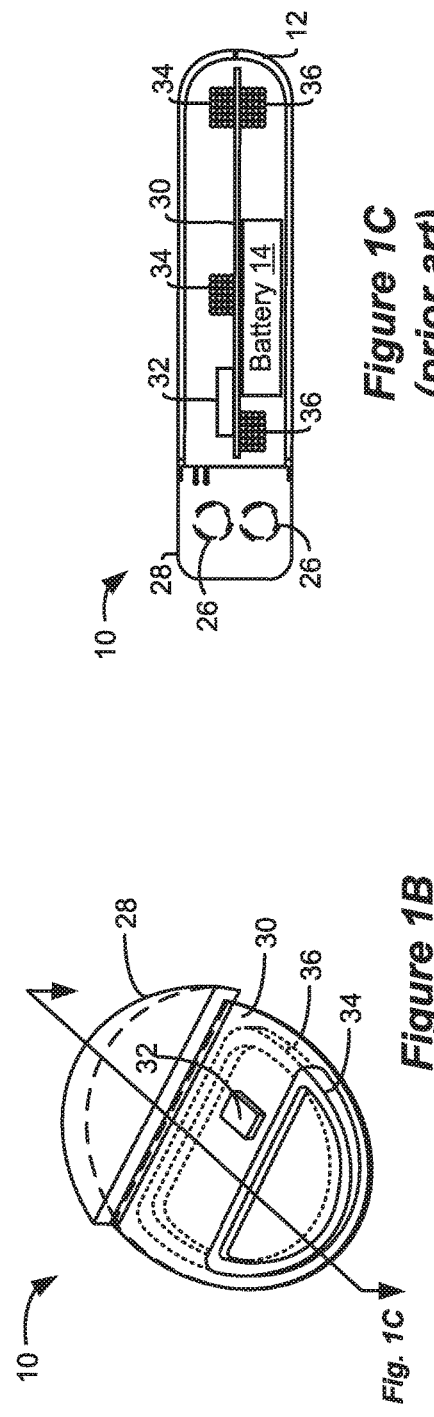
*Figure 1A (prior art)*
*Figure 1C (prior art)*
*Figure 1B (prior art)*

HOLDER FOR AN IMPLANTABLE MEDICAL DEVICE

CROSS REFERENCE TO RELATED APPLICATIONS

This is a non-provisional of U.S. Provisional Patent Application Ser. No. 62/362,943, filed Jul. 15, 2016, which is incorporated herein by reference in its entirety.

FIELD OF THE INVENTION

The present invention relates to a holder for an implantable medical device.

BACKGROUND

Implantable stimulation devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability in any implantable medical device system.

As shown in FIGS. 1A-1C, a SCS system typically includes an Implantable Pulse Generator (IPG) 10 (Implantable Medical Device (IMD) 10 more generally), which includes a biocompatible device case 12 formed of a conductive material such as titanium for example. The case 12 typically holds the circuitry and battery 14 (FIG. 1C) necessary for the IMD 10 to function, although IMDs can also be powered via external RF energy and without a battery. The IMD 10 is coupled to electrodes 16 via one or more electrode leads 18, such that the electrodes 16 form an electrode array 20. The electrodes 16 are carried on a flexible body 22, which also houses the individual signal wires 24 coupled to each electrode. In the illustrated embodiment, there are eight electrodes (Ex) on each lead 18, although the number of leads and electrodes is application specific and therefore can vary. The leads 18 couple to the IMD 10 using lead connectors 26, which are fixed in a non-conductive header material 28, which can comprise an epoxy for example.

As shown in the cross-section of FIG. 1C, the IMD 10 typically includes a printed circuit board (PCB) 30, along with various electronic components 32 mounted to the PCB 30, some of which are discussed subsequently. Two coils (more generally, antennas) are show in the IMD 10: a telemetry coil 34 used to transmit/receive data to/from an external controller (not shown); and a charging coil 36 for charging or recharging the IMD's battery 14 using an external charger, which is discussed in detail later.

FIG. 2 shows the IMD 10 in communication with an external charger 50 used to wirelessly convey power to the IMD 10, which power can be used to recharge the IMD's battery 14. The transfer of power from the external charger 50 is enabled by a primary charging coil 52. The external charger 50, like the IMD 10, also contains a PCB 54 on which electronic components 56 are placed. Again, some of these electronic components 56 are discussed subsequently. A user interface 58, including touchable buttons and perhaps a display and a speaker, allows a patient or clinician to operate the external charger 50. A battery 60 provides power for the external charger 50, which battery 60 may itself be rechargeable. The external charger 50 can also receive AC power from a wall plug. A hand-holdable housing 62 sized to fit a user's hand contains all of the components.

Power transmission from the external charger 50 to the IMD 10 occurs wirelessly and transcutaneously through a patient's tissue 25, via inductive coupling. FIG. 3 shows details of the circuitry used to implement such functionality. Primary charging coil 52 in the external charger 50 is energized via charging circuit 64 with an AC current, Icharge, to create an AC magnetic charging field 66. This magnetic field 66 induces a current in the secondary charging coil 36 within the IMD 10, providing a voltage across coil 36 that is rectified (38) to DC levels and used to recharge the battery 14, perhaps via a battery charging and protection circuitry 40 as shown. The frequency of the magnetic field 66 can be perhaps 125 kHz or so. When charging the battery 14 in this manner, is it typical that the housing 62 of the external charger 50 touches the patient's tissue 25, perhaps with a charger holding device or the patient's clothing intervening, although this is not strictly necessary.

The IMD 10 may also communicate data back to the external charger 50. For example, the IMD may use reflected impedance modulation, which is sometimes known in the art as Load Shift Keying (LSK). This involves modulating the impedance of the charging coil 36 with data bits ("LSK data") provided by the IMD 10's control circuitry 42 to be serially transmitted from the IMD 10 to the external charger 50. LSK communications are described further, for example in U.S. Patent Application Publication Nos. 2010/0305663 and 2013/0096652. Alternatively (or additionally), the IMD 10 may actively establish and conduct communication with the external charger 50 using Frequency Shift Keying (FSK), which is also well known in the art. With FSK the generated magnetic field is typically modulated. The induced voltage in coil 36 can then be demodulated at the IMD 10 back into the telemetered data signals. FSK is described in U.S. Pat. No. 9,364,672.

External charger 50 can also include one or more thermistors 71, which can be used to report the temperature (expressed as voltage Vtherm) of external charger 50 to its control circuitry 72, which can in turn control production of the magnetic field 66 such that the temperature remains within safe limits. See, e.g., U.S. Pat. No. 8,321,029, describing temperature control in an external charging device.

Vcoil across the external charger's charging coil 52 can also be assessed by alignment circuitry 70 to determine how well the external charger 50 is aligned relative to the IMD 10. This is important, because if the external charger 50 is not well aligned to the IMD 10, the magnetic field 66 produced by the charging coil 52 will not efficiently be received by the charging coil 36 in the IMD 10. Efficiency in power transmission can be quantified as the "coupling" between the transmitting coil 52 and the receiving coil 36 (k, which ranges between 0 and 1), which generally speaking comprises the extent to which power expended at the transmitting coil 52 in the external charger 50 is received at the receiving coil 36 in the IMD 10. It is generally desired that the coupling between coils 52 and 36 be as high as possible: higher coupling results in faster charging of the IMD battery 14 with the least expenditure of power in the external charger 50. Poor coupling is disfavored, as this will require high power drain (e.g., a high Icharge) in the external charger 50 to adequately charge the IMD battery 14. The use of high power depletes the battery 60 in the external charger 50, and more importantly can cause the external charger 50 to heat up, and possibly burn or injure the patient. Coupling between the transmitting and receiving coils is maximized when the coils are positionally aligned (i.e., the external coil is directly over the internal coil) and when the coils are parallel to each other.

BRIEF DESCRIPTION OF THE DRAWINGS

FIGS. 1A-1C show different views of an implantable pulse generator, a type of implantable medical device (IMD), in accordance with the prior art.

FIG. 2 shows an external charger being used to charge a battery in an IMD, while

DESCRIPTION

Figure 4A:
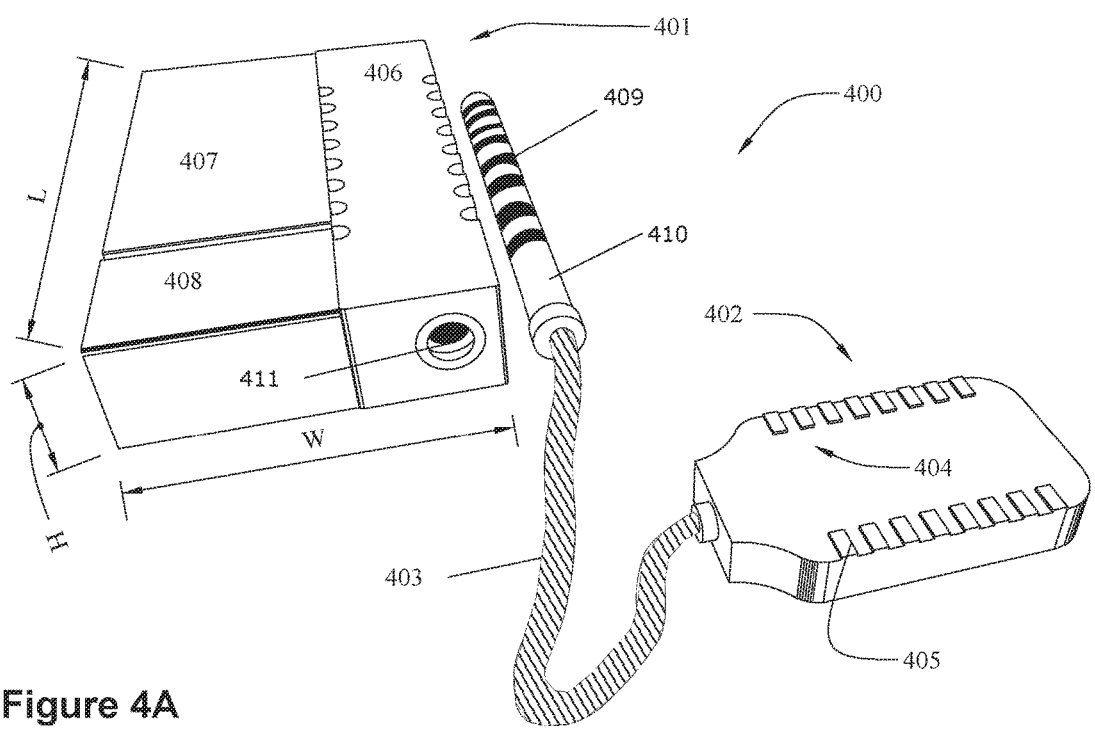
FIG. 4A-4B show views of a small volume IMD.

FIG. 4 shows an implantable medical device system 400 having an implantable medical device (IMD, more specifically, an implantable pulse generator) 401 connected to an electrode lead 402 by a cable 403. The electrode lead 402 supports an array 404 of electrodes 405. While the illustrated electrode lead 402 is box shaped, other shapes, such as the thin cylindrical leads 18 illustrated in FIG. 1A, are also possible. The electrodes 405 receive power from the IMD 401, which also controls which electrodes 405 are active at a given time.

Figure 4B:
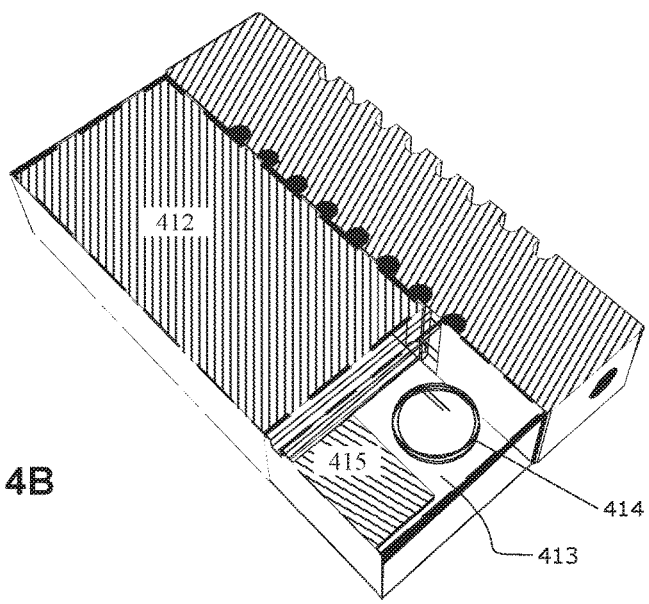

The illustrated IMD 401 includes a connector stack 406 that includes a receptacle 411 for connecting with a connector pin 410 attached to the cable 403. The connector stack 406 contains lead connectors (not shown) that contact mating conductors 409 on the connector pin 410 when the connector pin 410 is inserted into the receptacle 411. The lead connectors communicate with electronics within an electronics compartment 408 via feedthroughs (not shown). FIG. 4B shows the IMD 401 with the top cover made transparent to show the inside of the electronics compartment 408 and the battery compartment 407. The electronics compartment contains a printed circuit board (PCB) 413 upon which are mounted a coil 414 and electronic components 415. The battery compartment 407 contains a battery 412, which may be a rechargeable battery or a primary battery. The coil 414 can be used to inductively receive/transmit telemetry from an external controller and/or to receive power for charging the battery 412. The electronic components 415 can include a microprocessor and other components needed to operate and control the IMD 401.

The battery compartment 407 and the electronics compartment 408 typically include a biocompatible case formed of an electrically conductive material such as titanium for example. According to some embodiments, the battery compartment 407 and the electronics compartment 408 are contiguous, i.e., they are contained within the same case. Alternatively, they can comprise separate cases. According to some embodiments, the electrically conductive material acts as a counter electrode for the electrode(s) 405 of the electrode array 404. The contact stack 406 can be made from a non-conductive material such as medical-grade silicone or epoxy, for example.

According to some embodiments, the IMD has a total volume on the order of about 3 cubic centimeters. For example, the length (L) may be about 2 cm, the width (W) about 1.5 cm, and the height (H) about 1 cm. These dimensions are only an example and are not limiting.

Figure 5A:
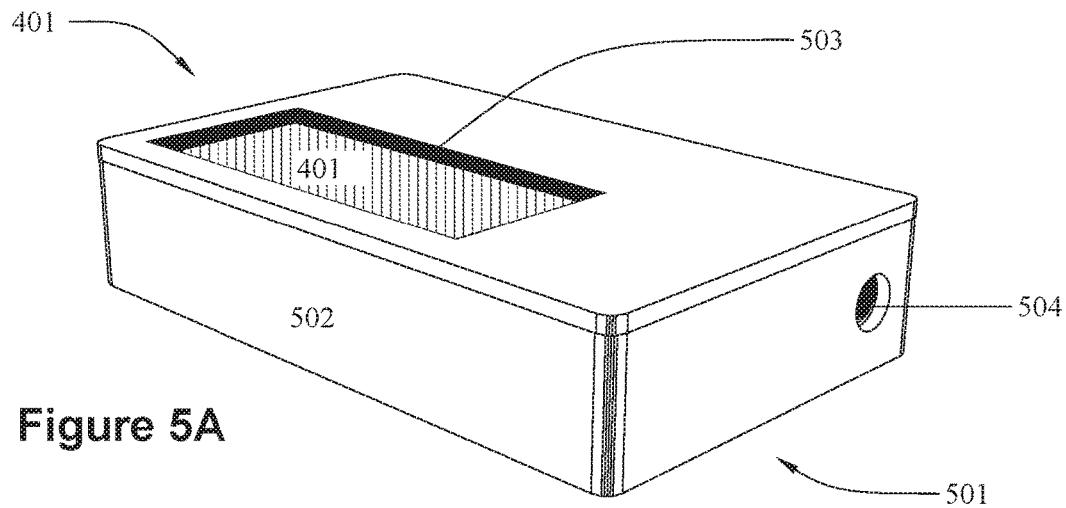
FIGS. 5A-5C show embodiments of a holder for an IMD.

FIG. 5A shows an embodiment of an IMD contained within a holder 501. The holder 501 comprises a sleeve, sock, or case structure 502 made of a biocompatible material such as medical-grade silicone or other biocompatible polymer materials. The holder 501 can be made using any medially acceptable manufacturing process, such as silicone injection molding, transfer/compression molding, etc. While the illustrated embodiment has distinct top and side portions, other embodiments may comprise more of a sleeve or sock configuration. The illustrated holder includes a window 503 to provide contact between a patient's tissue and the conductive case of the IMD 401 so that the case can act as a distant counter-electrode, as mentioned above. For example, the case of the IMD 401 covering the battery compartment 407 may be exposed. The holder also includes an opening 504 so that the connector pin 410 of the power cable 403 can access the receptacle 411 (see FIG. 4A).

Figure 5B:
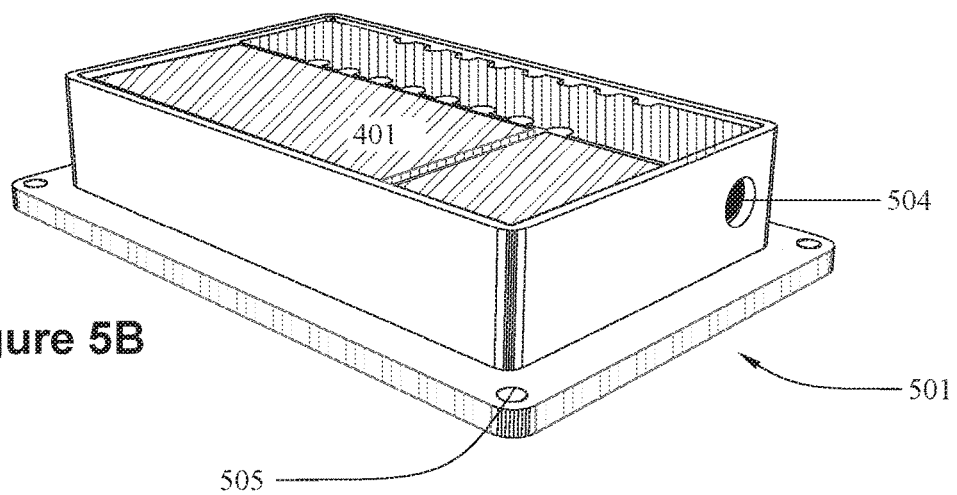

FIG. 5B shows another embodiment of a holder 501. The top is transparent only to illustrate how the IMD 401 is contained within the holder. Notice that the IMD 401 will only fit within the holder 501 in one way such that the opening 504 aligns with the receptacle 411. In other words, the holder 504 is "keyed" to insure proper alignment of the IMD 401. If the IMD 401 is not inserted into the holder 504 in the proper orientation, then the IMD will not be in an "operational orientation" when the holder and IMD are implanted in a patient.

Figure 5C:
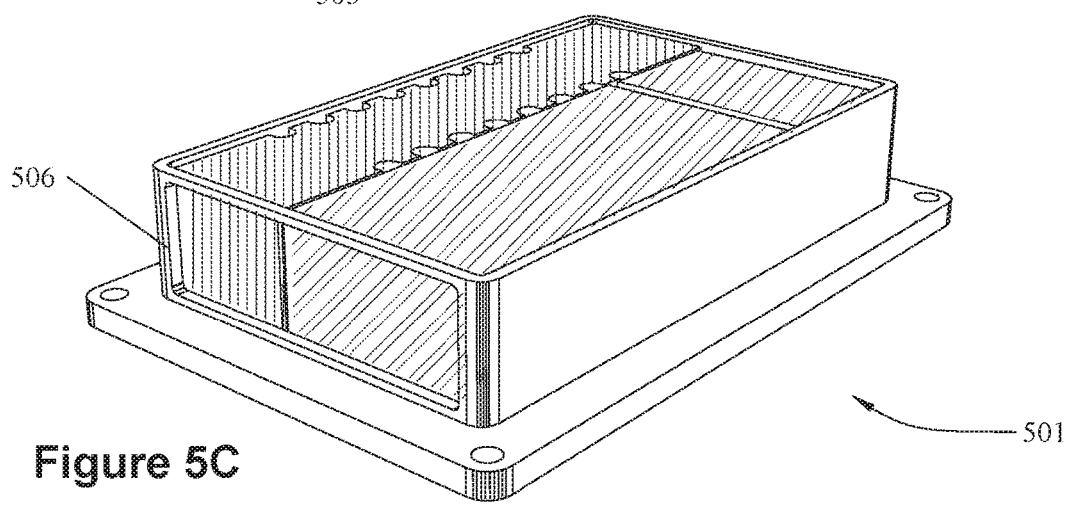

The holder 501 may optionally include suture loops, as illustrated in FIG. 5B, so that a physician can suture the holder 501 in place during implantation. FIG. 5C shows an alternate view of the embodiment illustrated in FIG. 5B. The holder 501 includes an opening 506 through which the IMD 401 can be inserted into the holder.

Figure 2:
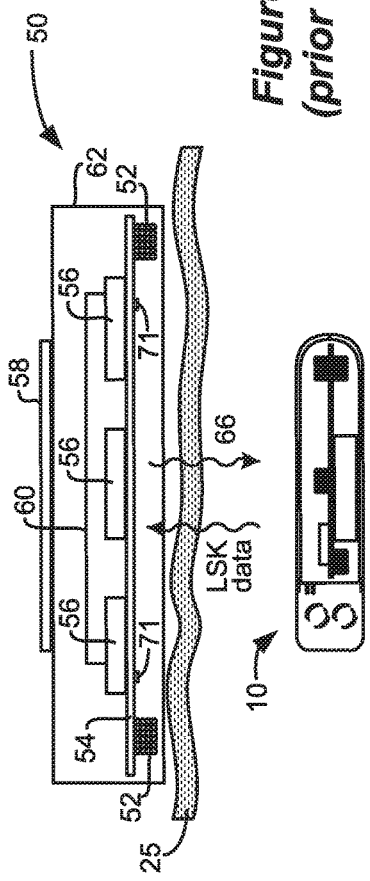
Figure 3:
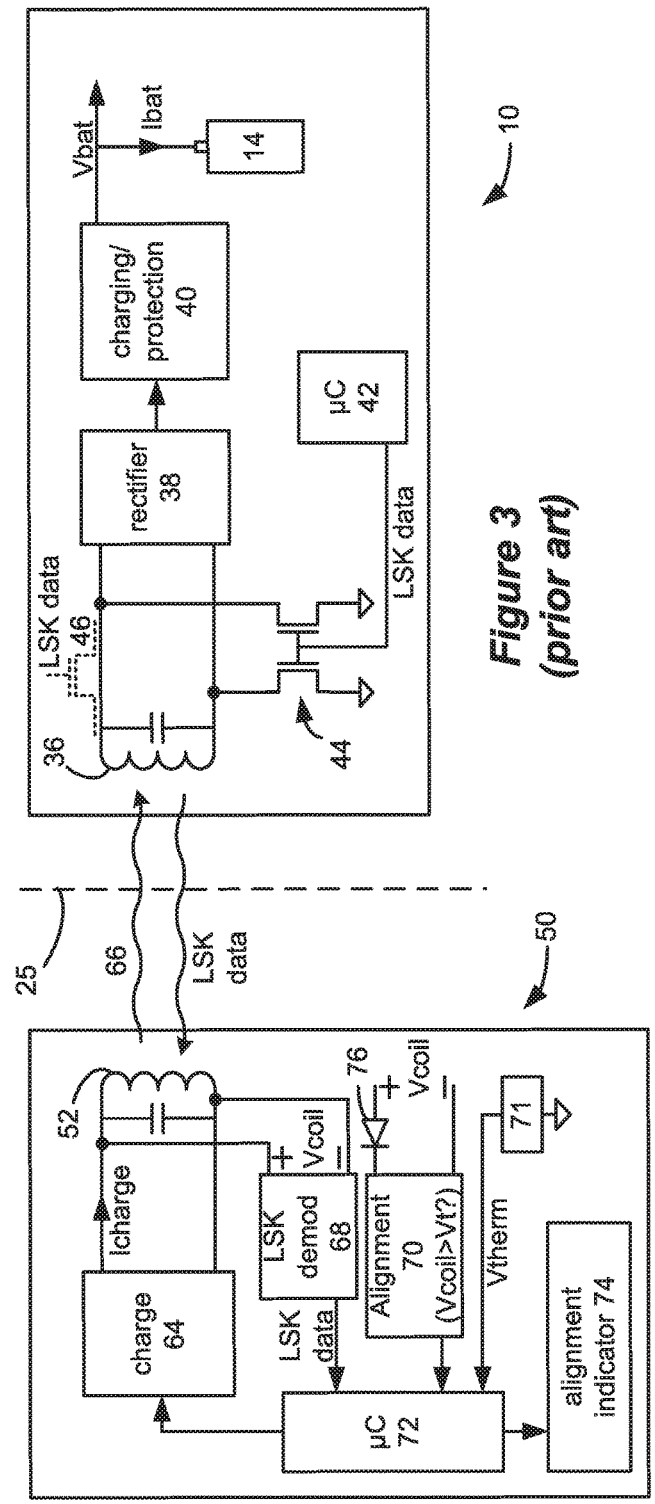
FIG. 3 shows circuitry in both, in accordance with the prior art.

The ability to "key" alignment of the of the IMD 401 and to suture the IMD in place is particularly helpful with regard to very small IMDs, which have a tendency to move once implanted. Such movement can lead to problems with charging the IMD and/or transmitting telemetry between the IMD and an external device because the coil 414 (FIG. 4) can become misaligned with the external device. As explained in the background section with reference to FIG. 2, communication of power 66 and telemetry (LSK data or FSK) between an implanted medical device 10 and an external device 50 relies on coupling between the coil 52 in the external device 10 and the coil 36 in the implanted device. Specifically, it is desirable that the coils be parallel to each other to maximize coupling. Very small IMDs such as IMD 401 are more prone to turning and moving and so are particularly prone to having the coil 414 become misaligned with an external device. Suturing the holder 501 in place addresses such misalignment.

Figure 6:
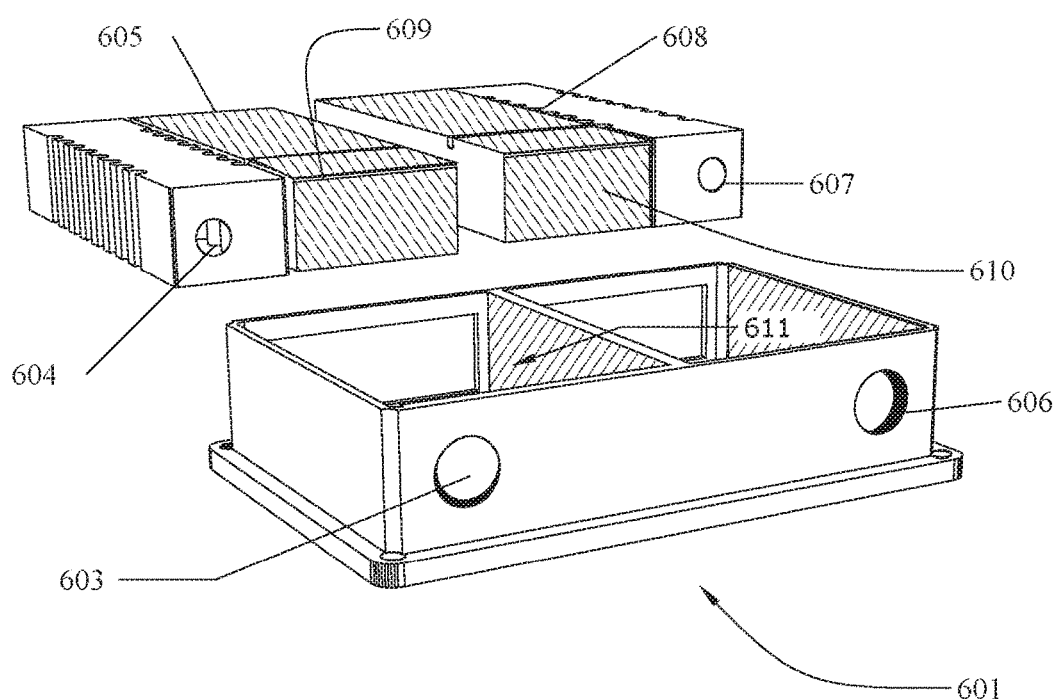
FIG. 6 shows a holder for holding a pair of IMDs.

FIG. 6 illustrates an embodiment of a holder 601 with compartments 611 for holding a pair 602 of IMDs. Again, the top is transparent for illustration only. The top may include a window, such as window 503 of FIG. 5A, to allow the cases of the IMDs to act as remote counter electrodes. The left opening 603 is arranged to align with the receptacle 604 of the left IMD 605 and the right opening 606 is arranged to align with the receptacle 607 of the right IMD 608. Therefore, the IMDs are only operational if the left IMD 605 is installed in the left side of the holder and the right IMD 608 is installed in the right side. If the IMDs are switched, then the openings and the receptacles will not line up correctly and the IMDs will not be operationally oriented when implanted in a patient. The left IMD will only fit properly within the left compartment and the right IMD will only fit within the right compartment. Thus, the holder 601 is keyed to insure proper placement and alignment of the IMDs with respect to each other. Moreover, in the illustrated embodiment the left and right electronics compartments (609 and 610, respectively) are aligned next to each other. Therefore, the coils of both the left IMD 605 and the right IMD 608 can simultaneously couple with a single external coil.

The ability to use multiple small IMDs allows the physician to tailor the size and capabilities of the total IMD resources to the patient. Even multiple small IMDs can be smaller than a single larger device of similar capabilities.

While the illustrated holder 601 accommodates two IMDs, alternative embodiments may include any number of IMDs. Also, while the illustrated holder 601 is a single piece capable of holding two IMDs, a dual (or more) IMD holder can alternatively be made by suturing together multiple single holders (for example, multiple holders such as holder 501 of FIGS. 5 B and C). Also, while the holders described herein are ideally suited for small-volume IMDs, they can also be scaled to hold conventionally sized IMDs.

The holders described herein are configured to key the IMDs into the proper alignment, both respect to other IMDs and with respect to an external coil for power and/or telemetry transfer. In the illustrated embodiments, the keying is provided by location of openings with the holder that must match with components of the IMD. However, other keying elements can be used. For example, the holder may include physical structures that are configured to mate with corresponding structures of the IMDs. Examples of such physical structures include matching features such as grooves or protrusions that mate the IMD within the holder in a lock-and-key fashion and only allow the IMD to fit properly within the holder in a single orientation.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover equivalents that may fall within the spirit and scope of the present invention as defined by the claims.

What is claimed is:

1. A medical device system, comprising:
an implantable medical device (IMD) comprising a receptacle configured to connect with a connecting pin of an electrode lead cable, wherein, when the connecting pin of the electrode lead cable is inserted into the receptacle, lead connectors within the IMD contact mating conductors of the connecting pin, and a holder comprising a compartment configured to hold the IMD, the holder further comprising an opening configured to allow the connecting pin to access the receptacle only when the IMD is contained within the holder in a keyed orientation;

wherein the IMD further comprises a housing comprising a conductive material and configured to operate as an electrode, and wherein the holder comprises a window configured to provide contact between the housing and tissue of the patient when the holder and the IMD are implanted in the patient.

2. The medical device system of claim 1, wherein the holder further comprises suture holes.

3. The medical device system of claim 1, wherein the IMD has a volume of less than or equal to 3 cm$^3$.

4. The medical device system of claim 1, wherein the IMD is a first IMD and the compartment is a first compartment, and wherein the medical device system further comprises a second IMD and wherein the holder comprises a second compartment configured to receive the second IMD.

5. The medical device system of claim 4, wherein the second IMD comprises a receptacle configured to connect with a connecting pin of a second electrode lead cable, wherein, when the connecting pin of the second electrode lead cable is inserted into the receptacle of the second IMD, lead connectors within the second IMD contact mating conductors of the connecting pin.

6. The medical device system of claim 5, wherein the holder further comprises a second opening configured to allow the connecting pin of the second electrode lead cable to access the receptacle of the second IMD only when the second IMD is contained within the holder in a second keyed orientation.

7. The medical device system of claim 4, wherein the holder maintains the first and second IMDs parallel to each other.

8. The medical device system of claim 4, wherein the first and second IMDs each comprise at least one coil, and wherein the holder is configured to maintain the coils parallel to each other.

9. The holder of claim 4, configured such that the first IMD will not operationally fit within the second compartment and the second IMD will not operationally fit within the first compartment.

* * * * *